United States Patent [19]

Hsu

[11] Patent Number: 4,575,564
[45] Date of Patent: Mar. 11, 1986

[54] CATALYST AND PROCESS FOR HYDROFORMYLATION OF OLEFINS

[75] Inventor: Chao-Yang Hsu, Media, Pa.

[73] Assignee: Sun Refining and Marketing Company, Philadelphia, Pa.

[21] Appl. No.: 707,277

[22] Filed: Mar. 1, 1985

Related U.S. Application Data

[62] Division of Ser. No. 598,933, Apr. 11, 1984, Pat. No. 4,528,278.

[51] Int. Cl.⁴ ............................................. C07C 45/50
[52] U.S. Cl. .................................... 568/454; 502/153
[58] Field of Search ................. 568/454, 909; 502/153

[56] References Cited

U.S. PATENT DOCUMENTS

| | | | |
|---|---|---|---|
| 4,138,420 | 2/1979 | Unruh | 568/454 |
| 4,139,565 | 2/1979 | Unruh | 568/454 |
| 4,155,939 | 5/1979 | Poist | 568/454 |
| 4,193,943 | 3/1980 | Unruh | 568/454 |
| 4,221,744 | 9/1980 | Unruh | 568/454 |
| 4,283,563 | 8/1981 | Kawabata | 568/454 |

Primary Examiner—Werren B. Lone
Attorney, Agent, or Firm—J. Edward Hess; Donald R. Johnson; Stanford M. Back

[57] ABSTRACT

Olefins are hydroformylated with syngas in the presence of a novel organo metallic complex catalyst to form the corresponding aldehydes at high reaction rates and improved selectivity of linear aldehydes over branched aldehydes.

The novel catalyst comprises an organo metallic complex formed from a mixture of:
(1) a platinum (II) compound;
(2) a ferrocene-derived ligand; and
(3) a Group IVB metal halide.

9 Claims, No Drawings

4,575,564

CATALYST AND PROCESS FOR HYDROFORMYLATION OF OLEFINS

This is a division of application Ser. No. 598,933, filed Apr. 11, 1984, now U.S. Pat. No. 4,528,278.

BACKGROUND OF THE INVENTION

1. Scope of the Invention

This invention relates to the process of hydroformylating olefins with syngas in the presence of a novel catalyst composition to form aldehydes. More particularly, it relates to an improved olefin hydroformylation catalyst system comprising (1) a mixture of a platinum (II) compound; a Group IVB metal halide; and a ferrocene—derived ligand, each of which components is described in further detail below.

The novel organometallic complex catalyst composition of this invention provides high reaction rates and high ratios of linear to branched aldehydes.

2. Description of the Prior Art

Processes of preparing aldehydes by hydroformylating an olefin with syngas, i.e., a mixture of hydrogen and carbon monoxide, in the presence of various catalysts, particularly cobalt and rhodium catalysts, is well known in the art. See, for example, Kirk-Othmer Encyclopedia of Chemical Technology ("OXO process"). Depending upon the catalyst, varying rates of reaction, and more importantly, different ratios of linear to branched aldehydes are obtained, the linear aldehydes being the preferred ones (as intermediates in the conversion, e.g., to alcohols by known hydrogenation methods and the like).

The use of platinum (II) compounds as hydroformylation catalysts in the OXO process, either alone, or in combination with $SnCl_2$, is known. Higher ratios of straight to branched aldehydes are obtained when tertiary phosphine-coordinated platinum complexes are used.

For example, $PtH(SnCl_3)(PPh_3)_2$ is shown by Hsu and Orchin, *J. Amer. Chem. Soc.*, 97 353 (1975) to be useful for conversion of 1-pentene to aldehydes. Schwager and Knifton, *J. Cat.*, 45, 256 (1976), U.S. Pat. No. 3,981,925 and U.S. Pat. No. 3,996,293 disclose use of $PtCl_2(PPh_3)_2 + SnCl_2$ for a similar reaction with 1-heptene. Kawabata, et al., J.C.S. *Chem. Comm* 462 (1979) teach $Pt(PhCN)_2Cl_2 + Ph_2P(CH_2)_xPPh_2$ for conversion of 1-pentene to aldehydes. U.S. Pat. Nos. 4,101,565 and 4,155,939 show the dimer $(PtCl_2PPh_3)_2 + SnCl_2$ for hydroformylation of 1-hexene. U.S. Pat. No. 3,876,672 also shows hydroformylation of 1-hexene with $PtH(PPh_3)_3 + HSO^-$. See also, U.S. Pat. No. 4,405,496, which describes a platinum (acetylacetonate) in combination with a Group IVA metal halide and a tertiary phosphine. Various arsenic, antimony, and phosphorus ligands derived from ferrocene in combination with rhodium catalysts are also known; see U.S. Pat. No. 4,138,420. Other effective platinum (II) compounds include the ionic complexes shown in U.S. Pat. No. 3,876,672.

Generally speaking, however, it is recognized that platinum complex-based hydroformylation catalysts usually give slower reaction rates compared to those of the early cobalt and rhodium catalysts. It is, therefore, an object of this invention to provide an olefin hydroformylation catalyst which both gives faster reaction rates, and also maintains a high selectivity for linear over branched aldehydes.

SUMMARY OF INVENTION

In accordance with the present invention there is provided a novel olefin hydroformylation organic metallic catalyst system comprising:

(1) a platinum (II) compound, the nature of which is not critical, but which may be selected from a wide range of platinum (II) compounds known in the art, and which typically have one of the following formulas:

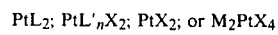
$PtL_2$; $PtL'_nX_2$; $PtX_2$; or $M_2PtX_4$ wherein L is a bidentate anion; L' is a monodentate or a bidentate unsaturated organic ligand, and n is 2 when the ligand is monodentate, or n is 1 when the ligand is bidentate; X is a halide, preferably chlorine; and M is an alkali metal;

(2) a ferrocene-derived ligand of the formula

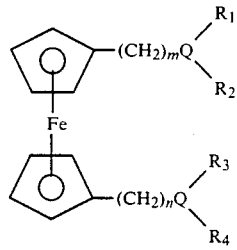

wherein Q is arsenic, antimony, or, most preferably, phosphorus; $R_1$, $R_2$, $R_3$ and $R_4$ are alkyl, aryl, alkoxyl, or aryloxyl, and wherein each of $R_1$, $R_2$, $R_3$ and $R_4$ can be the same or different; and m and n are integers of from 0 to 4; and (3) a Group IVB metal halide of the type previously used in the art but which typically may have one of the following formulas:

$MR_nX_{(4-n)}$; $MX_2$; or $MX_4$ wherein M is germanium, lead, or, most preferably, tin; R is alkyl, aryl, alkoxyl, or aryloxyl, in which case n is an integer of from 1 to 3, or R is an anion derived from a diketone, diacid, or diester, in which case n is an integer of from 1 to 3 if the anion is a mono-anion, or n is 1 if the anion is a di-anion; and X is a halide, preferably chlorine.

In the above formulas the R groups desirably contain one to six carbon atoms when alkyl, such as methyl, ethyl, or hexyl; or six to twenty carbon atoms when aryl, such as phenyl, naphthyl, tolyl or the like. Alkyl and alkoxyl groups include cycloalkyl and cycloalkoxyl while the aryl and aryloxyl groups include alkyl-substituted aromatic groups.

The invention is also directed the process of hydroformylating olefins with syngas in the presence of the aforedescribed catalysts to form aldehydes.

DESCRIPTION OF PREFERRED EMBODIMENTS OF THE CATALYST

The above-described catalyst of this invention is employed in a homogeneous system, the solvents for which may be selected from a wide range of solvents for the OXO reaction such as aromatic hydrocarbons, alkylaromatic hydrocarbons; alkyl, aryl, or alkylaryl ketones; or halogenated hydrocarbons. Illustrations of specific solvents include benzene, toluene, xylenes, ethylbenzene, tetralin, acetone, methylethyl ketone, acetophenone, dichloroethane, and the like.

The catalyst complexation may be accomplished separately, but is most conveniently prepared in situ by simply mixing together in the desired solvent the three aforesaid catalyst components, and thereafter carrying out the olefin hydroformylation process in a generally known manner. When combining these components, the ratios of the components, based on their metal content, are desirably in the range of about 0.5:1 to 20:1, and preferably less than 5:1 molar ratio for the [Group IVB metal]/[Pt]; and desirably in the range of from about 1:1 to 30:1, preferably less than 5:1 for the [P]/[Pt] molar ratio.

Although the reaction system is a homogeneous one, it has been found that the catalyst may readily be recovered and recycled with little or no loss of activity.

In the platinum complex, the bidentate anion L is desirably derived from a diketone, a diacid, or a diester, as for example an anion derived from acetylacetone, succinic acid, or dimethylmalonate.

The unsaturated monodentate or bidentate organic ligand L' is desirably derived from acetic acid or acetylacetone.

Examples of platinum (II) compounds which may be used as components of the catalyst include:
platinum (II) acetate [Pt(OAc)$_2$],
platinum (II) acetylacetonate [Pt(acac)$_2$],
bis-(benzonitrile) platinum (II) dichloride,
[Pt(C$_6$H$_5$CN)$_2$Cl$_2$],
bis-(acetonitrile) platinum (II) dichloride,
[Pt(CH$_3$CN)$_2$Cl$_2$],
1,5-cyclooctadiene platinum (II) dichloride,
[Pt(1,5-C$_8$H$_{12}$)Cl$_2$], and
norbornadiene platinum (II) dichloride [Pt(C$_7$H$_8$)Cl$_2$].

Examples of the ferrocene-derived ligands which may be employed include:
1,1'-bis-(diphenylphosphino)ferrocene
1,1'-bis-(diphenylphosphinomethyl)ferrocene
1,1'-bis-(diphenylphosphinoethyl)ferrocene
1,1'-bis-(diphenylphosphinopropyl)ferrocene,
as well as other aryl, alkyl or cycloalkyl equivalents, and the arsenic and antimony analogs thereof.

Examples of the Group IVB metal halides which may be employed include:
diphenyl tin(IV)dichloride [Sn(C$_6$H$_5$)$_2$Cl$_2$],
tin(IV)dichlorodiacetylacetonate [Sn(acac)$_2$Cl$_2$],
tin(II)dichloride [SnCl$_2$.2H$_2$O or SnCl$_2$],
tin(IV)tetrachloride [SnCl$_4$], and
phenyl tin(IV)trichloride [Sn(C$_6$H$_5$)Cl$_3$].

Illustrations of preferred combinations of the above three components used to form the catalysts complex of this invention are set forth in the examples below.

DESCRIPTION OF THE PROCESS

The hydroformylation of olefins with syngas in the presence of a catalyst is generally well-known (see the cited prior art-supra), and need not be repeated in detail herein.

Suffice it to say that the olefin starting material may be any olefin known in the art which can be hydroformylated. Examples of such olefins include $C_2$-$C_{20}$ aliphatic or cycloaliphatic monoolefins, and conjugated or non-conjugated aliphatic or cycloaliphatic diolefins, which preferably are linear, but which may branched and/or substituted, including such substituted olefins as ethylenically unsaturated alcohols, aldehydes, ketones, esters and the like, as well as aromatic compounds whose ethylenically unsaturated side chain is capable of being hydroformylated such as styrene or allylbenzene. Where mixtures of olefins are employed, the process of this invention nevertheless generally results in the selective formation of linear aldehydes in major yields.

The reaction conditions are those generally employed in the art, and may vary widely depending upon the olefin and catalyst employed, but which typically include temperatures of from about 25°–125° C., preferably 75°–100° C.; pressures of from about 100–3000 psi, preferably 750–1500 psi; and a syngas ratio of H$_2$/CO desirably in the range of from about 0.25 to 4, and more preferably 0.75 to 2.0 (molar ratio).

Finally, the concentration of catalyst complex employed in the reaction, based on the amount of metallic platinum in the complex, which may vary widely, is desirably in the range of from about $1 \times 10^{-5}$ to $1 \times 10^{-1}$ mole, and more preferably $1 \times 10^{-3}$ to $2 \times 10^{-2}$ mole, per mole of olefin present.

The hydroformylation process may be conducted in a batch, semi-continuous or continuous manner. Moreover, the process can be combined with hydrogenation of the aldehydes to alcohols by venting the reactor after aldehyde formation and introducing hydrogen under suitable conditions of temperature and pressure. The catalyst used for the hydroformylation can also be used for the hydrogenation or fresh catalyst can be added. Less preferably, the reactor is not vented and a large volume of hydrogen is introduced for admixture with syngas remaining from the hydroformylation.

The invention will now be illustrated by, but is not intended to be limited to, the following examples.

EXAMPLE 1

To a 300 ml stainless steel autoclave reactor was added 100 ml of p-xylene as a solvent, 0.5 mmole of Pt(acac)$_2$, 2.5 mmole of SnCl$_2$.2H$_2$O, and 0.5 mmole of 1,1'-bis(diphenylphosphino)ferrocene (DPFE). After the mixture was stirred for 10 minutes under a nitrogen atmosphere, the autoclave was sealed and purged with syngas (H$_2$/CO=1:1) twice, and then charged syngas to about 500 psi. The autoclave was then quickly heated to 100° C., whereupon 250 mmole of propylene was charged, and the reaction pressure was increased to 1000 psi with syngas. After one hour of reaction time (under 1000 psi of snygas, and at 100° C.), heating was stopped and the reaction mixture in the autoclave was cooled to room temperature. The gas phase materials were vented. The liquid phase was removed from the autoclave and analyzed directly by the use of vapor phase chromatography. Analysis of the reaction mixture indicated that 82% yield of butyraldehydes was obtained and the molar ratio of straight chain n-butyraldehyde to branched chain iso-butyraldehyde was 7.77 (i.e., 88.6% of straight chain n-butyraldehyde). The results are shown in Table I.

EXAMPLES 2–3

A series of runs was carried out according to the same procedure set forth above in Example 1, except the platinum (II) acetylacetonate [(Pt(acac)$_2$] was replaced by another platinum (II) compound. The results are listed in Table I. The relative reaction rates, based on the consumption of syngas, were determined by leaving the reaction shown in Example 1 as a standard reaction (i.e., relative rate=1).

EXAMPLES 4–9

A series of runs was carried out according to the same procedure as described in Example 1, except the reaction conditions were changed. The results are shown in Table II.

TABLE I

HYDROFORMYLATION OF PROPYLENE WITH VARIOUS Pt(II) COMPLEXES[1]

| EXAMPLE | Pt(II) COMPOUND (mmole) | TIN HALIDE (mmole) | DPFE[4] (mmole) | RELATIVE RATE | n/iso[3] |
|---|---|---|---|---|---|
| 1 | Pt(acac)$_2$ (0.50) | SnCl$_2$.2H$_2$O (2.50) | 0.50 | 1.0 | 7.77 |
| 2 | Pt(COD)Cl$_2$[2] (0.50) | SnCl$_2$.2H$_2$O (2.50) | 0.50 | 0.83 | 7.40 |
| 3 | Pt(C$_6$H$_5$CN)$_2$Cl$_2$ (0.50) | SnCl$_2$.2H$_2$O (2.50) | 0.50 | 1.13 | 7.40 |

[1] The reactions were conducted under the following conditions: propylene 250 mmole, solvent (p-xylene) 100 ml, 1000 psi of syngas pressure (H$_2$/CO = 1:1), 100° C.
[2] Pt(1,5-cyclooctadiene)Cl$_2$
[3] n/iso = n-butyraldehyde/iso-butyraldehyde ratio.
[4] DPFE = 1,1'-BIS-(Diphenylphosphino)Ferrocene

TABLE II

HYDROFORMYLATION OF PROPYLENE UNDER VARIOUS REACTION CONDITIONS[1]

| EXAMPLE | Pt(acac)$_2$ (mmole) | TIN HALIDE (mmole) | DPFE (mmole) | RELATIVE RATE | n/iso[7] |
|---|---|---|---|---|---|
| 4[2] | 0.50 | SnCl$_2$.2H$_2$O (2.50) | 0.50 | 0.62 | 7.33 |
| 5[3] | 0.50 | SnCl$_2$.2H$_2$O (2.50) | 0.50 | 1.30 | 8.17 |
| 6[4] | 0.50 | SnCl$_2$.2H$_2$O (2.50) | 0.50 | 0.89 | 8.01 |
| 7[5] | 0.50 | SnCl$_2$.2H$_2$O (2.50) | 0.50 | 1.53 | 4.30 |
| 8 | 0.50 | Sn(C$_6$H$_5$)$_2$Cl$_2$ (2.50) | 0.50 | 1.63 | 7.47 |
| 9[6] | 0.50 | SnCl$_2$.2H$_2$O (2.50) | 0.50 | 2.30 | 7.47 |

[1] Unless indicated otherwise, the reaction was conducted under the following standard conditions: propylene 250 mmole, solvent (p-xylene) 100 ml, 1000 psi of syngas pressure (H$_2$/CO = 1:1) 100° C.
[2] 750 psi
[3] 1500 psi
[4] 1250 psi
[5] 110° C.
[6] 110° C., 1500 psi
[7] n/iso = n-butyraldehyde/iso-butyraldehyde

EXAMPLE 10

In accordance with the procedures of Example 1, except that 1-butene is substituted for propylene, there is obtained linear 1-pentanal in good yield and selectivity over the corresponding branched aldehyde.

In a like manner, but substituting 1-pentene for propylene and Sn(C$_6$H$_5$)Cl$_3$ for SnCl$_2$.2H$_2$O the corresponding linear 1-hexanal is obtained in good yield and selectivity.

EXAMPLE 11

In accordance with the procedures of Example 2, but substituting 2-pentene for propylene, and Sn(C$_6$H$_5$)$_2$Cl$_2$ for SnCl$_2$.2H$_2$O, there is obtained the linear 1-hexanal in good yield and selectivity over the corresponding branched aldehyde.

In a like manner, but substituting styrene for propylene, the corresponding linear 3-phenylpropanel is obtained in good yield and selectivity.

EXAMPLE 12

In accordance with the procedures of Example 3, but substituting α-methylstyrene for propylene, and SnCl$_4$ for SnCl$_2$.2H$_2$O there is obtained linear 3-phenylbutyraldehyde in good yield and selectivity over the corresponding branched aldehyde.

In a like manner, but substituting allylbenzene for propylene, and Pt(C$_6$H$_5$CN)$_2$Cl$_2$ for Pt(acac)$_2$ the corresponding linear 4-phenylbutyraldehyde is obtained in good yield and selectivity.

EXAMPLE 13 (PRIOR ART)

This example illustrates the hydroformylation of propylene to butyraldehyde in the presence of a prior art platinum-phosphorus-tin complex catalyst in a manner similar to that disclosed in U.S. Pat. No. 3,981,925.

To a 300 ml stainless steel autoclave was added 100 ml of toluene as solvent, 0.53 g (1.0 mmole) of PtCl$_2$(PPh$_3$)$_2$, 1.14 g (5.0 mmole) of SnCl$_2$.2H$_2$O, and 1.31 g (5.0 mmole) of PPh$_3$. After the mixture was stirred for 15 minutes under a nitrogen atmosphere, the autoclave was purged with syngas (H$_2$/CO=1:1) and 10.5 g (250 mmole) of propylene was added. The autoclave was then charged with syngas (H$_2$/CO=1:1) to make a total pressure of 750 psig. After which the reactor was then quickly heated to 100° C. and the syngas pressure was maintained at 1000 psig through constant addition of syngas from a reservoir. After 4 hours of reaction, the autoclave was cooled to room temperature and the gas phase materials were vented. The liquid contents were removed and analyzed directly by vapor phase chromatography. Analysis of the reaction mixture indicated that 85% yield of butyraldehydes was obtained and the molar ratio of n-butyraldehydes to iso-butyraldehyde was 6.7 (i.e., 87% of normal aldehyde).

From a comparison of the results set forth in Tables I and II with those of comparative Example 13, it will be seen that significant improvements in the reaction rates; i.e., about a 4-fold increase, together with improvements in n/iso ratios of n- to iso-aldehyes, are obtained with the catalyst system of this invention.

What we claim is:

1. In the process of hydroformylating an olefin by reacting the olefin with hydrogen and carbon monoxide at elevated pressures in the presence of a catalyst to produce an aldehyde, the improvement of using as the catalyst a catalyst system which comprises (1) Pt(acetylacetonate)$_2$,; (2) a ferrocene-derived ligand; and (3) a Group IVB metal halide.

2. The process of claim 1 wherein the ferrocene-derived ligand is of the formula:

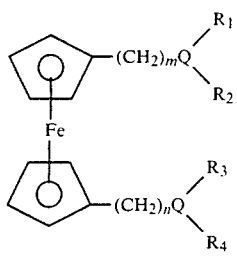

wherein Q is antimony, arsenic, or phosphorus; $R_1$, $R_2$, $R_3$ and $R_4$ are alkyl, aryl, alkoxyl, or aryloxyl, and wherein each of $R_1$, $R_2$, $R_3$ and $R_4$ may be the same or different; and m and n are integers of from 0 to 4.

3. The process of claim 1 wherein the Group IVB metal halide is of the formula:

$MR_nX_{(4-n)}$; $MX_2$; or $MX_4$ wherein M is germanium, lead, or, most preferably, tin; R is alkyl, aryl, alkoxyl, or aryloxyl, in which case n is an integer of from 1 to 3, or R is an anion derived from a diketone, diacid, or diester, in which case n is an integer of from 1 to 3 if the anion is a mono-anion, or n is 1 if the anion is a di-anion; and X is a halide.

4. The process of claim 1 wherein the concentration of catalyst, based on the amount of metallic platinum in the complex, is from about $1 \times 10^{-5}$ to $1 \times 10^{-1}$ mole, per mole of olefin present.

5. The process of claim 1 wherein the molar ratio of the Group IVB metal to platinum is in the range of about 0.5:1 to 20:1 and the ratio of phosphorus to platinum is in the range of from about 1:1 to 30:1.

6. The process of claim 1 wherein; the ferrocene-derived ligand is 1,1'-bis(diphenylphosphino)ferrocene; and the Group IVB metal halide is $SnCl_2.2H_2O$.

7. The process of claim 1 wherein; the ferrocene-derived ligand is 1,1'-bis(diphenylphosphino)ferrocene; and the Group IVB metal halide is $Sn(C_6H_5)_2Cl_2$.

8. The process according to claim 1 wherein the olefin is propylene, 1-butene, 1-pentene, 2-pentene, styrene, α-methylstyrene, or allylbenzene.

9. The process according to claim 1 wherein the olefin has from about 2 to 20 carbon atoms.

* * * * *